United States Patent
Xie

(10) Patent No.: US 10,173,089 B2
(45) Date of Patent: Jan. 8, 2019

(54) POLY-PERFLUOROALKYL SUBSTITUTED POLYETHYLENEIMINE FOAM STABILIZERS AND FILM FORMERS

(71) Applicant: Tyco Fire Products LP, Lansdale, PA (US)

(72) Inventor: Yuan Xie, Marinette, WI (US)

(73) Assignee: Tyco Fire Products LP, Lansdale, PA (US)

( * ) Notice: Subject to any disclaimer, the term of this patent is extended or adjusted under 35 U.S.C. 154(b) by 331 days.

(21) Appl. No.: 14/775,558

(22) PCT Filed: Mar. 14, 2014

(86) PCT No.: PCT/US2014/029174
§ 371 (c)(1),
(2) Date: Sep. 11, 2015

(87) PCT Pub. No.: WO2014/153122
PCT Pub. Date: Sep. 25, 2014

(65) Prior Publication Data
US 2016/0030793 A1  Feb. 4, 2016

Related U.S. Application Data

(60) Provisional application No. 61/785,963, filed on Mar. 14, 2013.

(51) Int. Cl.
| | |
|---|---|
| *A62D 1/02* | (2006.01) |
| *C07F 7/08* | (2006.01) |
| *C08K 5/41* | (2006.01) |
| *C07C 309/69* | (2006.01) |
| *C07C 303/30* | (2006.01) |
| *C08K 5/3475* | (2006.01) |
| *C08K 5/12* | (2006.01) |
| *C08K 5/17* | (2006.01) |
| *C09K 3/18* | (2006.01) |
| *C08L 79/02* | (2006.01) |
| *C08G 73/02* | (2006.01) |

(52) U.S. Cl.
CPC ......... *A62D 1/0085* (2013.01); *A62D 1/0071* (2013.01); *C07C 303/30* (2013.01); *C07C 309/69* (2013.01); *C07F 7/0838* (2013.01); *C07F 7/0889* (2013.01); *C08G 73/0206* (2013.01); *C08K 5/12* (2013.01); *C08K 5/17* (2013.01); *C08K 5/3475* (2013.01); *C08K 5/41* (2013.01); *C08L 79/02* (2013.01); *C09K 3/18* (2013.01)

(58) Field of Classification Search
CPC ... A62D 1/0085; A62D 1/0071; C07F 7/0854; C07F 7/0889; C07C 303/30; C07C 309/69; C08K 5/41; C08K 5/12; C08K 5/17; C08K 5/3475; C09K 3/18; C08G 73/0206; C08L 79/02
See application file for complete search history.

(56) References Cited

U.S. PATENT DOCUMENTS

| | | | |
|---|---|---|---|
| 3,422,011 A | 1/1969 | Jackovitz et al. | |
| 3,457,172 A | 7/1969 | Stewart et al. | |
| 3,579,446 A | 5/1971 | Kroke et al. | |
| 3,957,657 A | 5/1976 | Chiesa, Jr. | |
| 4,060,132 A | 11/1977 | Chiesa, Jr. | |
| 4,060,489 A | 11/1977 | Chiesa, Jr. | |
| 4,306,979 A | 12/1981 | Tsuji | |
| 4,387,032 A | 6/1983 | Chiesa, Jr. | |
| 4,420,434 A | 12/1983 | Falk | |
| 4,424,133 A | 1/1984 | Mulligan | |
| 4,464,267 A | 8/1984 | Chiesa et al. | |
| 4,536,298 A | 8/1985 | Kamei et al. | |
| 5,207,932 A | 5/1993 | Norman et al. | |
| 5,218,021 A | 6/1993 | Clark et al. | |
| 5,616,273 A | 4/1997 | Clark et al. | |
| 5,750,043 A * | 5/1998 | Clark ................... | A62D 1/0085 252/2 |
| 9,669,246 B2 | 6/2017 | Bowen et al. | |
| 9,956,447 B2 | 5/2018 | Martin et al. | |
| 9,956,448 B2 | 5/2018 | Martin | |
| 2003/0201419 A1* | 10/2003 | Tanaka ................. | A62D 1/0057 252/3 |
| 2013/0277597 A1 | 10/2013 | Bowen et al. | |

FOREIGN PATENT DOCUMENTS

WO  WO 96/05889 A1  2/1996

OTHER PUBLICATIONS

International Search Report and Written Opinion, International Application No. PCT/US2014/029174 (published as WO 2014/153122) (dated Jul. 24, 2014).

* cited by examiner

*Primary Examiner* — Peter F Godenschwager
*Assistant Examiner* — Andrew J. Oyer
(74) *Attorney, Agent, or Firm* — Foley & Lardner LLP

(57) ABSTRACT

Poly-perfluoroalkyl substituted polyethyleneimine compositions are provided that act as foam stabilizers and film formers when used in fire-fighting foam concentrates. The polyethylene compositions are soluble in water, but have only low solubility in polar solvents. When aqueous film forming foam generated from these concentrates is applied to burning polar solvent the polyethyleneimine compositions precipitate at the polar solvent/foam interface and inhibit the collapse and destruction of the foam.

9 Claims, No Drawings

POLY-PERFLUOROALKYL SUBSTITUTED POLYETHYLENEIMINE FOAM STABILIZERS AND FILM FORMERS

PRIORITY DATA

This application is a 35 U.S.C. § 371 application of International Application No. PCT/US2014/029174, filed Mar. 14, 2014, which claims the benefit of U.S. Provisional Patent Application No. 61/785,963, filed Mar. 14, 2013, each of which application is incorporated herein by reference in its entirety.

BACKGROUND

Perfluoroalkyl surfactants are commonly used in the preparation of aqueous fire-fighting foams (AFFFs). These surfactants are effective when used in preparing foams used to extinguish fires caused by non-polar fuels such as hydrocarbons, and act by covering the surface of the burning fuel with a vapor-suppressing film. However, such foams are ineffective in fighting fires caused by polar solvents, such as alcohols, ketones, or tetrahydrofuran, because the foam is destroyed by mixing with the water-miscible fuel.

To address this problem, so-called alcohol-resistant fire-fighting foams (AR-AFFFs) have been developed. AR-AFFF formulations contain water-soluble polymers that prevent the foam from collapsing on polar fuels and that also significantly lengthen the foam drain time by increasing the viscosity of the aqueous phase. The polymers most commonly used are polysaccharides such as xanthan and rhamsan gums. The dissolved gum precipitates from the foam solution when it contacts the polar fuel and forms a soft mat, or membrane, between the foam blanket and fuel to block further intermixing. However, the high concentrations of polysaccharide gums necessary to make an effective AR-AFFF concentrate can cause the concentrate to be so thick that the concentrate is difficult to pump efficiently, and therefore can cause proportioning problems during foam generation and application. The use of certain fluoropolymer surfactants has the same polar fuel performance as xanthan gums, but with much lower viscosity increase. See, for example, U.S. Pat. No. 6,156,222. Therefore, a significant portion of the gum can be replaced by fluoropolymer surfactants to give better AR-AFFF performance.

SUMMARY OF THE INVENTION

Foam stabilizers are provided containing a highly branched substituted polyamine where the amino groups of the polyamine are substituted with (a) —$(CH_2)_m(CF_2)_nF$, where m is 1-12 and n is 4-16; and (b) a hydrophilic moiety selected from the group consisting of —$(CH_2)_pCHOH(CH_2)_qSO_3^-$, $(CH_2)_pCHOH(CH_2)_qNH_4^+$ and $(CH_2)_pCOO^-$; where p and q independently are 1-6 and p+q is 2-8. The substituted polyamine has an average molecular weight $M_w$ of between about 5 kDa and 25 kDa prior to substitution; and the stabilizer has a fluorine content of about 15 to about 25%. The amino groups of the polyamine may be further substituted with a siloxane moiety such as $(R_3SiO)_2Si(R)(CH_2)_3OCH_2CHOHCH_2$— or $R_3SiO[Si(R)_2O]_rSi(CH_2)_3OCH_2CHOHCH_2$-, where each R independently is lower alkyl, r=1-9, and where the stabilizer has a silicon content of about 0.1 to about 10%. In certain embodiments, n may be 4-6, for example, or may be 6. In some embodiments m may be 1 or 2, and in certain embodiments may be 1 or 2. In specific embodiment, p and q may be 1 or 2.

In some embodiments, the weight average molecular weight $M_w$ of the unsubstituted polyamine is about 10 kDa.

Also provided are methods of making a highly branched substituted polyamine, by reacting a highly branched polyamine having an average molecular weight $M_w$ of between about 5 kDa and 25 kDa with (i) X—$(CH_2)_m(CF_2)_nF$, where m is 1-12 and n is 4-16 and (ii) a hydrophobic moiety selected from the group consisting of X—$(CH_2)_pCHOH(CH_2)_qSO_3^-$, X—$(CH_2)_pCHOH(CH_2)_qNH_4^+$ and X—$(CH_2)_pCOO^-$; where p and q independently are 1-6 and p+q is 2-8; and where each X independently is a leaving group that can be displaced by an amine, and where the resulting stabilizer has a fluorine content of about 15 to about 25%. A siloxane moiety may optionally be added to the polymer by reacting the highly branched polyamine with a siloxane moiety selected from the group consisting of

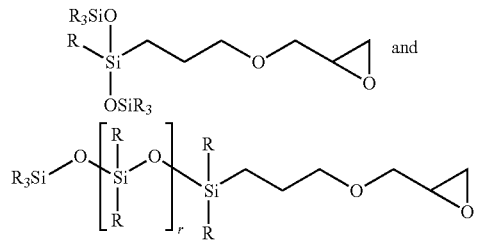

where each R independently is lower alkyl, and r=1-9.

Also provided are aqueous film-forming firefighting composition concentrates containing (a) an effective amount of a foam stabilizing agent as described above. The concentrate may further contain (b) an effective amount of a monomeric perfluoroalkyl surfactant, and/or (c) an effective amount of at least one non-fluorinated surfactant. The composition optionally may further contain an effective amount of one or more components selected from the group consisting of: a foam aid, a freeze protection composition, a composition containing ion sequestering, buffer, and anti-corrosion components, a biocide and antimicrobial composition, an electrolyte composition, and a polysaccharide gum thickener.

Fire-fighting foams also are provided, containing a foam stabilizer or composition as described above, together with methods of making such foams by foaming a composition as described above with an aqueous liquid, such as liquids containing fresh water, brackish water and salt water. Methods of fighting fires by contacting a fire with these foams are provided.

DETAILED DISCLOSURE

Novel water-soluble polymers are provided that are useful as foam stabilizers and film forming agents in firefighting foams. The novel polymers have low solubility in polar solvents and improve the stability of firefighting foams when the foams are used to fight fires fueled by such polar solvents. In addition, when these foams are applied to fires fueled by polar solvents the polymers precipitate from the foam and form a liquid or solid film at the polar solvent/foam interface. This precipitate significantly delays the collapse and destruction of the foam, thereby enhancing the fire extinguishing and burnback resistance properties of the foam.

Also provided are AR-AFFF firefighting concentrates and compositions containing the novel polymers. The presence of the novel polymers in these compositions permits the use of lowered amounts of polysaccharide film-forming gums, and even allows use of compositions that lack gums altogether. Lowering or removing the gum concentration in this fashion significantly reduces the viscosity of the compositions, which allows the compositions to be proportioned more easily and more accurately than conventional AR-AFFF compositions.

Structure of the Polymers

The novel polymers are branched polyamines containing a mixture of primary, secondary and tertiary amines in which the amine groups are substituted with at least two types of substituent: (a) a perfluoroalkyl moiety that is both oleophobic and hydrophobic and a (b) hydrophilic group. Optionally, the amine groups may further be substituted with (c) a siloxane moiety that acts as a foam rolling booster. Advantageously, the polyamine is a polyethyleneimine ("PEI") although other branched polyamines also could be used.

The polyamine composition used to prepare the novel polymers is a highly branched polymer. Suitable polyamines are commercially available aliphatic polyamines prepared by polymerization of amines such as diethylenetriamine, triethylenetetramine, tetraethylenepentamine, pentaethylenehexamine, aminoethylpiperazine, and 2 iminobispropylamine. Suitable polyamines can be prepared from these and other amines by methods that are well known in the art.

Advantageously the polyamine is a PEI having a ratio of primary, secondary and tertiary amines that is about 1:2:1, although the skilled artisan will recognize that this is not an absolute requirement, and that PEI compositions with differing ratios also can be used. The starting polyamine can have a molecular weight of from about 800 to about 25,000, advantageously 5000 to 25000, before it is derivitized, although, again, the skilled artisan will recognize that polymers with molecular weights outside this range may also be used if desired. In the context of the starting polyamine and the novel polymers, "molecular weight" refers to the weight average molecular weight $M_w$). Suitable starting polyamine compositions are, for example, PEI polymers available commercially from, for example, SigmaAldrich (St. Louis, Mo.) and Nippon Shokubai (as Epomin®)

The novel polymers described herein comprise a highly branched substituted polyamine where the amino groups of the polyamine are substituted with (a) a perfluoroalkyl moiety having the structure $—(CH_2)_m(CF_2)_nF$; and (b) a hydrophilic moiety, where the hydrophilic moiety is selected from the group consisting of $—(CH_2)_pCHOH(CH_2)_qSO_3^-$, $(CH_2)_pCHOH(CH_2)_qNH_4^+$ and $(CH_2)_pCOO^-$. In hydrophobic moiety (a), m can be 1-12, advantageously 1-6 or 1-2 and n can be 4-16, advantageously 4-8 or 4-6. In hydrophilic moiety (b) p and q independently can be 1-6, advantageously 1-3 or 1-2, and p+q is 2-8, advantageously 2-4.

The starting polyamine has an average molecular weight $M_w$ of about 800 to 25,000, advantageously about 5000 to 25000, or 10,000 to 15,000, prior to substitution. After substitution the polymer advantageously has a fluorine content of between about 15% and about 25%, although a variation of 10% above and below these values also is acceptable. In the context of the present polymers the fluorine content is determined by a calculation based on 100% conversion of perfluoroalkyl alkyl iodide starting material and by fluorine elemental analysis). The relative molar ratios of starting polymer, hydrophobic perfluoroalkyl moiety, hydrophilic moiety and siloxane moiety can vary as desired, but advantageously are in the ranges shown:

| Polymer | Siloxane moiety | Perfluoroalkyl moiety | Hydrophilic moiety |
|---------|----------------|----------------------|-------------------|
| 10-50   | 0-0.5          | 1                    | 1-5               |

Novel polyamine polymers containing the hydrophobic and hydrophilic substituents described above can be used as foam stabilizers without further substitution. Alternatively, a siloxane substituent can be added to the polymer. Suitable siloxane moieties include those having the formula $(R_3SiO)_2Si(R)(CH_2)_3OCH_2CHOHCH_2—$ or $R_3SiO[Si(R)_2O]_rSi(CH_2)_3OCH_2CHOHCH_2-$, where each R independently is lower alkyl, r=1-9, and where the stabilizer has a silicon content of about 0.1 to about 10%. In the context of the present polymers, the term "lower alkyl" means $C_1$-$C_6$ alkyl, advantageously $C_1$-$C_4$ alkyl, and where the alkyl group can be straight chain or branched. Advantageously the siloxane moiety can be $(Me_3SiO)_2Si(Me)(CH_2)_3OCH_2CHOHCH_2—$ or $n-C_4H_9Si(CH_3)_2O[Si(CH_3)_2O]_rSi(CH_2)_3OCH_2CHOHCH_2—$, or mixtures of both.

Preparation of the Polymers

The polymers may conveniently be prepared by nucleophilic substitution of the amine groups of the polymer using suitable alkylating agents. Thus, for the perfluoroalkyl and hydrophilic substituents the polymer can be reacted with reagents containing well-known leaving groups such as halogen atoms, tosylate, mesylate and triflate groups and the like.

Advantageously the perfluoroalkyl moiety is introduced by reacting the polymer with a perfluoroalkyl alkyl halide, more advantageously a perfluoroalkyl alkyl iodide. Suitable perfluoroalkyl reagents include those with the general structure $X—(CH_2)_m(CF_2)_nF$, where m is 1-12 and n is 4-16 and X is a leaving group that can be displaced by an amine, such as iodide.

The hydrophilic moiety similarly is introduced by contacting the polymer with a reagent having a structure selected from $X—(CH_2)_pCHOH(CH_2)_qSO_3^-$, $X—(CH_2)_pCHOH(CH_2)_qNH_4^+$ and $X—(CH_2)_pCOO^-$, where p and q independently are 1-6, p+q is 2-8, and X is a leaving group that can be displaced by an amine. Advantageously X in the hydrophilic reagent is chloride, bromide or iodide The siloxane moiety is advantageously introduced via the ring-opening reaction of an epoxide. Thus, the polymer can be reacted with a siloxane moiety selected from

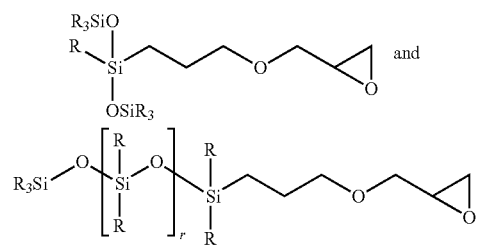

where each R independently is lower alkyl, advantageously $C_1$-$C_6$ alkyl and more advantageously $C_1$-$C_4$ alkyl, and r=1-9.

The alkylation reactions can be carried out simultaneously or sequentially. Advantageously, the reactions are carried out sequentially and conveniently in a single reaction vessel. Thus, the starting polyamine can first be reacted with a perfluoroalkyl alkyl iodide, followed by reaction with the hydrophilic reagent described above. The reaction is carried out in any suitable non-reactive solvent in which the reagents are soluble. Advantageously, isopropanol ("IPA") can be used. In a typical reaction scheme the starting polymer and perfluoroalkyl alkyl halide are heated in IPA, for example at 70° C., for a period of time sufficient to consume all of the alkylating agent. The hydrophilic reagent is then introduced and the resulting mixture heated again to 70° C. until the hydrophilic reagent is consumed. Alternatively, the order of reaction can be reversed, with the hydrophilic reagent added first, followed by the perfluoroalkyl alkyl halide.

When the siloxane moiety is to be introduced into the polymer, the siloxane epoxide reagent can be added in any order to the reaction mixture, but typically is added either last, or simultaneously with the reagent added second. Again the ring-opening of the epoxide can be carried out in the same solvent as the alkylation reactions used to introduce the perfluoroalkyl and hydrophilic moieties.

After the alkylation reactions are complete, the solvent can be removed in vacuo and/or by atmospheric distillation) and the resulting polymer typically is used without further purification. However, if desired, the polymer product may be further purified using methods well known in the art, for example, size exclusion chromatography, ion-exchange chromatography and the like.

Compositions Containing the Polymers

The polymers as described above can be used to prepare aqueous firefighting composition concentrates that are effective for preparing alcohol-resistant aqueous film-forming foams. Specifically, the polymers can be used to prepare AR-AFFF concentrates using methods that are known in the art and the polymers described herein can be used to replace some or all of the high molecular weight polymers used in the concentrates known in the art. See for example, U.S. Pat. No. 5,750,043, the contents of which are hereby incorporated by reference in their entirety.

Concentrates prepared from the polymers described herein are useful for extinguishing UL162 Class B polar (water soluble) and non-polar (water insoluble) liquid fuel fires. The concentrates also meet the standards set forth in EN 1568-3 an EN 1568-4. Methods for determining the effective amount of polymer for use in the concentrates are well known in the art.

Advantageously, concentrates containing the polymers described above also contain an effective amount of a monomeric perfluoroalkyl surfactant, and an effective amount of at least one non-fluorinated surfactant. The concentrates also may contain one or more components such as a foam aid, a freeze protection composition, a composition comprising ion sequestering, buffer, and anti-corrosion components, a biocide and antimicrobial composition, an electrolyte composition, and a polysaccharide gum thickener.

The AR-AFFF concentrates may be produced at any suitable strength, including, but not limited to, 1, 3 and 6% (w/w) foam concentrates, which are concentrations that are typical for commercial use. Concentrates that are less than 1% (w/w) or greater than 6% (w/w) also may be prepared. As used herein, the lowest numbered strength for the concentrate used indicates the most concentrated product, i.e., the percent designation refers to the proportioning rate of foam concentrate to water. Accordingly, one part of 1% concentrate used with 99 parts water gives 100 parts of use strength pre-mix; similarly, three parts 3% concentrate and 97 parts water gives 100 parts of pre-mix. As used herein, the term "water" may include pure, deionized or distilled water, tap or fresh water, sea water, brine, or an aqueous or water-containing solution or mixture capable of serving as a water component for the fire-fighting composition.

Typical components used for preparing AR-AFFF concentrates are shown in the tables below, together with typical % concentrations (w/w).

A, 1×1 AR-AFFF:

| Component | Weight % |
|---|---|
| Fluorosurfactant | 4~8% |
| Polyamine polymer (fluorine containing) | 12~18% |
| Decyl sulfate (surfactant) | 1~4% |
| Lauryl Dipropionate (surfactant) | 1~4% |
| Ethylene glycol (freeze protection) | 15~30% |
| Tolytriazole (corrosion inhibitor) | 0.02~0.06% |
| Butyl carbitol (solvent, foam stabilizer) | 5~10% |
| Water | balanced to 100% |
| Fluorosurfactants | 2~6% |
| Polyamine polymer | 1~4% |
| Alkyl polysaccharide (surfactant?) | 2~6% |
| Alkyl sulfo-betaine (surfactant) | 1~5% |
| Decyl sulfate (surfactant) | 1~5% |
| Magnesium sulfate (electrolyte) | 1~3% |
| Tolytriazole (corrosion inhibitor) | 0.01~0.05% |
| Dowicil 75 (antimicrobial) | 0.01~0.04% |
| Kelco K1A112 (rhamsan gum) | 0.4~2.0% |
| Water | balanced to 100% |

B, LV 3×3 AR AFFF:

| Component | Weight % |
|---|---|
| Fluoro surfactants | 2~6% |
| Polyamine polymer | 1~4% |
| Alkyl polysaccharide (surfactant?) | 2~6% |
| Alkyl sulfo-betaine (surfactant) | 1~5% |
| Decyl sulfate (surfactant) | 1~5% |
| Magnesium sulfate (electrolyte) | 1~3% |
| Tolytriazole (corrosion inhibitor) | 0.01~0.05% |
| Dowicil 75 (antimicrobial) | 0.01~0.04% |
| Kelco K1A112 (rhamsan gum) | 0.4~2.0% |
| Water | balanced to 100% |

The above components would be reduced or increased accordingly relative to the 3% liquid concentrate to prepare 6% and 1% synthetic liquid foam concentrates, or other concentrate levels. Thus, for a 1% concentrate, the above amounts may be increased by a factor of 3, whereas for a 6% concentrate the above amounts may be reduced by half.

Fluoropolymer Component

The high molecular weight fluoropolymers as described herein may be used in an amount to provide a foam concentrate that may have from about 0.005% or less to about 6% or more fluorine by weight of concentrate, more typically from about 0.01% to about 4.5% fluorine by weight of concentrate. The final fire-fighting foam or composition may have fluorine content of from about 0.0003% to about 0.065% fluorine by weight of solution, advantageously from about 0.0006% to about 0.05% by weight fluorine from the fluoropolymers being typical, or from 0.001% to about 0.035% by weight fluorine.

The amounts of fluorine from the fluoropolymer will vary in the concentrate depending upon the type of concentrate employed. Thus a 3% concentrate may have from about 0.01% by weight fluorine to about 2% by weight fluorine from the fluoropolymer, advantageously from about 0.02% to about 1.5% by weight, or from about 0.05% to about 1% by weight. A 1% foam concentrate may have from about 0.03% to about 6% by weight fluorine from the fluoropolymer, advantageously from about 0.06% to about 4.5% by weight fluorine being typical, or from about 0.15% to about 3% by weight fluorine. A 6% concentrate may have from about 0.005% to about 1% by weight fluorine from the fluoropolymer, advantageously from about 0.01% to about 0.5% by weight fluorine, or from about 0.025% to about 0.4% by weight fluorine.

Hydrocarbon (Non-Fluorinated) Surfactants

Amphoteric hydrocarbon surfactants include, but are not limited to, those which contain in the same molecule, amino and carboxy, sulfonic, and sulfuric ester moieties and the like. Higher alkyl ($C_6$-$C_{14}$) betaines and sulfobetaines are included in this category. Commercially available products include Chembetaine CAS (Lubrizol Inc.) and Mirataine CS (Rhodia), both sulfobetaines, and Deriphat 160C (BASF), a $C_{12}$ amino-dicarboxylate. These products are foaming agents and help reduce interfacial tension in water solution.

Anionic hydrocarbon surfactants include, but are not limited to, alkyl carboxylates, sulfates, sulfonates, and their ethoxylated derivatives. Alkali metal and ammonium salts are suitable. $C_8$-$C_{16}$ hydrocarbon surfactants are suitable, including, advantageously, $C_8$-$C_{10}$.

Nonionic hydrocarbon surfactants help reduce interfacial tension and solubilize other components, especially in hard water, sea water or brine solutions. They also serve to control foam drainage, foam fluidity, and foam expansion. Suitable nonionic surfactants include, but are not limited to, polyoxyethylene derivatives of alkylphenols, linear or branched alcohols, fatty acids, alkylamines, alkylamides, and acetylenic glycols, alkyl glycosides and polyglycosides, as defined in U.S. Pat. No. 5,207,932 (herein incorporated by reference) and others, and block polymers of polyoxyethylene and polyoxypropylene units.

Fluorocarbon Surfactants

Fluorochemical surfactants are typically single perfluorotail molecules and may have multiple hydrophilic heads. Advantageously, the fluorochemical surfactant contains perfluoroalkyl groups no longer than $C_6$, although $C_8$ and longer fluorosurfactants can also be used. Examples of suitable fluorochemical surfactants include those described in WO/2012/045080.

The quantity of fluorochemical surfactant(s) may be added to increase extinguishing speed and burnback resistance. The presence of the fluoropolymers described herein permits the total fluorochemical surfactant content to be less than one-half of the typical workable levels required when the fluorinated polymers are absent while still meeting UL162 Class B and EN 1568 fire performance. The fluorosurfactant may provide less than about 0.2% or 0.1% fluorine in a 3% concentrate, or less than about 0.006% or 0.003% fluorine, respectively, at the working strength. Fluorine content provided by any fluorosurfactant in the final or working fire-fighting composition may be less than 0.002% or even 0.001% fluorine by weight of the working composition.

Foam Aids

Foam aids may be used to enhance foam expansion and drain properties, while providing solubilization and antifreeze action. Useful foam aids are well known in the art and are disclosed, for example, in U.S. Pat. Nos. 5,616,273, 3,457,172; 3,422,011 and 3,579,446, which are herein incorporated by reference.

Typical foam aids include alcohols or ethers such as ethylene glycol monoalkyl ethers, diethylene glycol monoalkyl ethers, propylene glycol monoalkyl ethers, dipropylene glycol monoalkyl ethers, triethylene glycol monoalkyl ethers, 1-butoxyethoxy-2-propanol, glycerine, and hexylene glycol.

Freeze Protection Package

A freeze protection package is used to prevent the concentrate freezing or becoming unusably viscous at low temperatures. Typical components include glycerine, ethylene glycol, diethylene glycol, and propylene glycol. Other potential components include salts and other solids which reduce the freezing point of the concentrate, such as calcium, potassium, sodium and ammonium chloride and urea.

Sequestering, Buffer, and Corrosion Package

The components of the sequestering, buffer, and corrosion package, include agents that sequester and chelate metal ions. Examples include polyaminopolycarboxylic acids, ethylenediaminetetraacetic acid, citric acid, tartaric acid, nitrilotriacetic acid, hydroxyethylethylenediaminetriacetic acid and salts thereof. Buffers are exemplified by Sorensen's phosphate or McIlvaine's citrate buffers. The nature of the corrosion inhibitors is limited only by compatibility with other formula components. Typical corrosion inhibitors include ortho-phenylphenol, toluyl triazole, and many phosphate ester acids.

Polymeric Film Former

These water-soluble polymeric film formers, dissolved in AR-AFFF agents, precipitate from solution when the bubbles contact polar solvents and fuel, and form a vapor-repelling polymer film at the solvent/foam interface, preventing further foam collapse. Examples of suitable compounds include thixotropic polysaccharide gums as described in U.S. Pat. Nos. 3,957,657; 4,060,132; 4,060,489; 4,306,979; 4,387,032; 4,420,434; 4,424,133; 4,464,267, 5,218,021, and 5,750,043, which are herein incorporated by reference. Suitable commercially available compounds are marketed as Rhodopol, Kelco, Keltrol, Actigum, Cecal-gum, Calaxy, and Kalzan.

Gums and resins useful as film formers include acidic gums such as xanthan gum, pectic acid, alginic acid, agar, carrageenan gum, rhamsam gum, welan gum, mannan gum, locust bean gum, galactomannan gum, pectin, starch, bacterial alginic acid, succinoglucan, gum arabic, carboxymethylcellulose, heparin, phosphoric acid polysaccharide gums, dextran sulfate, dermantan sulfate, fucan sulfate, gum karaya, gum tragacanth and sulfated locust bean gum.

Neutral polysaccharides useful as film formers include: cellulose, hydroxyethyl cellulose, dextran and modified dextrans, neutral glucans, hydroxypropyl cellulose, as well, as other cellulose ethers and esters. Modified starches include starch esters, ethers, oxidized starches, and enzymatically digested starches.

Antimicrobials and Preservatives

These components may be used to prevent biological decomposition of natural product based polymers incorporated as polymeric film formers. Examples include Kathon CG/ICP (Rohm & Haas Company) and Givgard G-4 40 (Givaudan, Inc.), and are disclosed in U.S. Pat. No. 5,207,932, which is herein incorporated by reference. Additional preservatives are disclosed in U.S. Pat. Nos. 3,957,657; 4,060,132; 4,060,489; 4,306,979; 4,387,032; 4,420,434; 4,424,133; 4,464,267, 5,218,021, and 5,750,043.

Electrolytes

Electrolytes may be added to AR-AFFF agents to balance the performance of such agents when proportioned with water ranging from soft to very hard, including sea water or brine, and to improve agent performance in very soft water. Typical electrolytes include salts of monovalent or polyvalent metals of Groups 1, 2, or 3, or organic bases. The alkali metals particularly useful are sodium, potassium, and lithium, or the alkaline earth metals, especially magnesium, calcium, strontium, and zinc or aluminum. Organic bases might include ammonium, trialkylammonium, bis-ammonium salts or the like. The anions of the electrolyte are not critical, except that halides may not be desirable due to metal corrosion. Sulfates, bisulfates, phosphates, nitrates and the like are commonly used. Examples of polyvalent salts include magnesium sulfate and magnesium nitrate.

Polymeric Foam Stabilizers and Thickeners

Concentrates containing fluoropolymers of the type described herein typically do not contain additional polymeric foam stabilizers and thickeners, but such components may be included if desired. These components can be optionally incorporated to enhance the foam stability and foam drainage properties. Examples of polymeric stabilizers and thickeners include partially hydrolyzed protein, starches, polyvinyl resins such as polyvinyl alcohol, polyacrylamides, carboxyvinyl polymers, polyvinyl polypyrrolidone, and poly(oxyethylene) glycol.

High MW perfluorinated polymers of the type described herein may be used with commercially available synthetic surfactant concentrates to prepare foam concentrates. The commercially available surfactant concentrates are marketed worldwide and include those available from Chemguard, Kidde, and Tyco. These products include: Class A foams (CLASS A PLUS and SILVEX), excellent for extinguishing forest fires, structural fires, and tire fires; high expansion foams sold under the names HI-EX, EXTRA, C2, and VEE-FOAM; vapor suppressant foam sold by Chemguard as VRC foam; bomb foam, a 6% product sold by Chemguard as AFC-380.

Synthetic surfactant concentrates listed as "wetting agents" by Underwriters Laboratory may also be included as base surfactant mixtures for preparing AR-AFFF concentrates. Products listed by UL as "wetting agents" are as follows: Fire Strike by Biocenter Inc.; Bio-Fire by Envirorenu Technologies LLC; Enviro-Skin 1% by Environmental Products Inc.; F-500 by Hazard Control Technologies Inc.; Knockdown by National Foam Inc.; Phos-Chek WD881 by Solutia Inc.; Flameout by Summit Environmental Corp. Inc. Micro-Blazeout by Verde Environmental Inc.; Bio-solve by Westford Chemical Corp.

Use of AR-AFFF Concentrates

Concentrate prepared as described above may be mixed with water, typically as a 3% solution, and foamed using foaming devices well known in the art. As water under pressure passes through a fire hose, typically 3 percent by volume of the concentrate composition is inducted into the hose line by the Venturi effect to form a foam solution of the concentrate diluted with water. The solution becomes aerated to produce finished foam by use of an air-aspirating nozzle located at the outlet end of the hose. A foam solution stored for any length of time prior to aeration is known as a foam premix and can likewise be aerated to produce a finished foam. Equipment which can be used to produce and apply these aqueous air-foams are known in the art and also are described in publications by the National Fire Protection Association.

The concentrate, upon dilution with water and aeration, produces an aqueous film-forming foam which is applied to a body of flammable liquid such as a spill or pool which is burning or subject to ignition. The foam extinguishes the burning liquid, and prevents further ignition by providing a blanket to cover the fuel surface and excluding air.

Preferably, the compositions are introduced into a fire or flame in an amount sufficient to extinguish the fire or flame. One skilled in the art will recognize that the amount of extinguishing composition needed to extinguish a particular hazard will depend upon the nature and extent of the hazard.

EXAMPLES

Example 1

Preparation of Substituted Highly Branched Polyamine Containing Hydrophobic Perfluoroalkyl and Hydrophilic Substituents

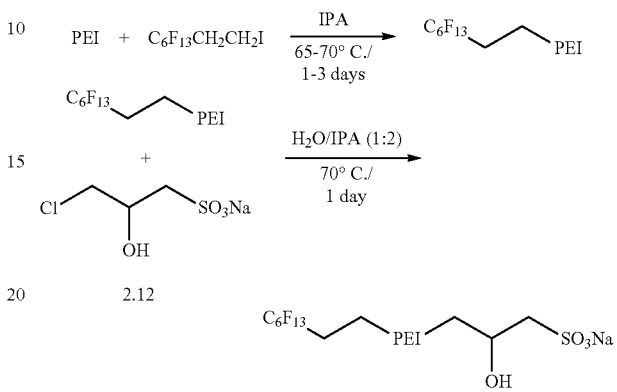

A one-pot, two step conversion was used to prepare a highly substituted PEI. Briefly, a highly branched PEI was first reacted with a perfluoro alkyl iodide, and the resulting product was then reacted with 3-chloro-2-hydroxy-propanesulfonic acid without purification of the intermediate product to provide the final highly substituted PEI.

Exemplary Reaction Procedure:

To a 500 ml three necked round bottom flask equipped with a thermometer, a magnetic stirrer and condenser was added a branched PEI ($M_w$~10,000, 31.7 g, 0.74 mol, monomer-based molarity), 1H,1H,2H,2H-perfluorooctane iodide (25.7 g, 0.054 mol), and isopropyl alcohol (IPA, 160 ml). The mixture was heated to 65~70° C. with stirring under an inert atmosphere for 1~3 days, after which a solution of 3-chloro-2-hydroxy-propanesulfonic acid, sodium salt (27 g, 0.13 mol) in water (80 ml) was added. The mixture was stirred at 70° C. for one additional day under an inert atmosphere, and then was evaporated in vacuo or atmospheric distillation to remove most of the IPA and to provide the desired polymer at a concentration of ~40%. The fluorine content of the polymer was measured as ~18.74%, and the calculated $M_w$ of the substituted polymer was ~22,500 based on complete consumption of the reagents. This material was used without further separation or purification for preparing a foam concentrate as described in Example 2.

Example 2

Use of Highly Branched Polyamine in Preparing Foam Concentrate

A substituted PEI prepared according to Example 1 was tested in a firefighting concentrate and compared to two commercially available firefighting concentrates. Ansulite LV 3×3 and Ansulite 1×1 ARC are commercially available concentrates that contain a matched high molecular weight polymer as a foam stabilizer. Formulations were prepared that were identical to Ansulite LV 3×3 and Ansulite 1×1 ARC except that the high molecular weight polymer present in the commercial formulations was replaced with the same fluorine weight amount of the polymer from example 1. The resulting formulations achieved the same fire suppression performance and matched all the other desired physical properties of these commercial products).

Example 3

Preparation of Substituted Highly Branched Polyamine Containing Hydrophobic Perfluoroalkyl, Hydrophilic and Siloxane Substituents

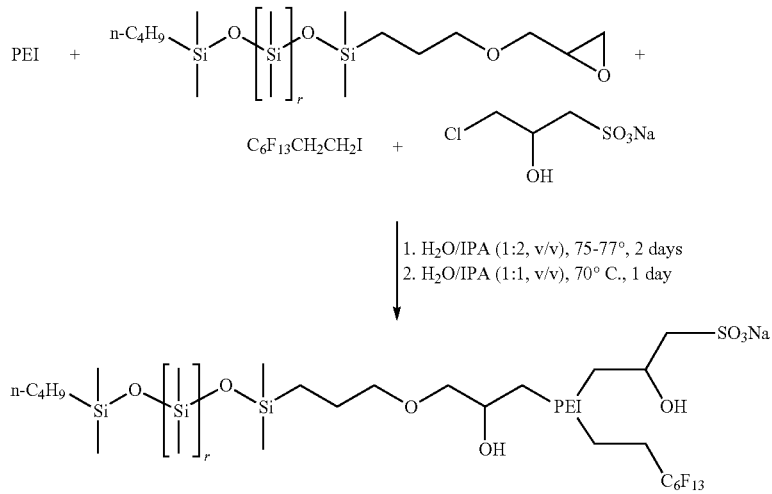

A polymer containing hydrophobic, hydrophilic and siloxane substituents was prepared via a two step conversion in a one pot reaction as summarized in the reaction scheme above. Briefly, to a 500 ml three necked round bottom flask equipped with a thermometer, a magnetic stirrer and condenser was added a branched PEI ($M_w$~1,800, 21.5 g, 0.5 mol, monomer-based molarities), 1H,1H,2H,2H-perfluorooctane iodide (2.82 g, 0.00595 mol), polydimethylsiloxane, diglycidyl ether terminated ($M_w$~980) (5.84 g, 0.00595 mol), $H_2O$ (60 ml) and isopropyl alcohol (IPA, 145 ml). The mixture was heated to 65~70° C. with stirring under an inert atmosphere for 1~3 days, after which a solution of 3-chloro-2-hydroxy-propanesulfonic acid, sodium salt (3.66 g, 0.0.0178 mol) in water (80 ml) was added. The mixture was stirred at 70° C. for one additional day under an inert atmosphere, and then was evaporated in vacuo or by atmospheric distillation to remove most of the IPA and to provide the desired polymer at a concentration of ~40%)

The calculated fluorine content ~12.49% (wt %) and the calculated $M_w$ was ~21,700, where both values were calculated based on assumed total conversion of reagents.

Foam quality of the polymer was assessed on an aqueous solution at a concentration of 0.2 g(F)/1 L of $H_2O$. Hexylene glycol (2 g) was added and the resulting solution was agitated in a blender to make foam. Foam expansion was measured on 100 ml of the solution against its foam volume and drainage time was also measured simultaneously at 50% of its drainage liquid.

Foam quality of this sample with around 40% solid content was: FE(ml): 240 ml; 50% DT(m's"): 1'50";

The stability of foams containing this polymer was also assessed in a 1×1 ARC formulation as described above, and the stability was shown to be comparable while reducing the fluorine content by 50%.

What is claimed is:

1. An aqueous film-forming firefighting composition comprising an effective amount of a foam stabilizing agent comprising a branched substituted polyamine wherein the amino groups of said polyamine are substituted with:

(a) —$(CH_2)_m(CF_2)_nF$, wherein m is 1-12 and n is 4-16; and
(b) a hydrophilic moiety selected from the group consisting of
—$(CH_2)_pCHOH(CH_2)_qSO_3^-$,
$(CH_2)_pCHOH(CH_2)_qNH_4^+$ and
$(CH_2)_pCOO^-$; wherein p and q independently are 1-6 and p+q is 2-8;

wherein said substituted polyamine has a weight average molecular weight $M_w$ of between about 5 kDa and 25 kDa prior to substitution; and wherein said stabilizer has a fluorine content of about 15 to about 25%.

2. The aqueous film-forming firefighting composition according to claim 1 further comprising: an effective amount of a monomeric perfluoroalkyl surfactant; and an effective amount of at least one non-fluorinated surfactant.

3. The aqueous film-forming firefighting composition according to claim 1 further comprising an effective amount of one or more components selected from the group consisting of: a foam aid; a freeze protection composition; a composition comprising ion sequestering, buffer, and anticorrosion components; a biocide and antimicrobial composition; an electrolyte composition; and a polysaccharide gum thickener.

4. The aqueous film-forming firefighting composition according to claim 1, wherein said amino groups of said polyamine are further substituted with a siloxane moiety selected from the group consisting of $(R_3SiO)_2Si(R)(CH_2)_3OCH_2CHOHCH_2$— and $R_3SiO[Si(R)_2O]_rSi(CH_2)_3OCH_2CHOHCH_2$—, wherein each R independently is lower alkyl, r=1-9, and wherein said foam stabilizing agent has a silicon content of about 0.1 to about 10%.

5. The aqueous film-forming firefighting composition according to claim 1 wherein n is 4-6.

6. The aqueous film-forming firefighting composition according to claim 5, wherein n is 6.

7. The aqueous film-forming firefighting composition according to claim 1, wherein m is 1 or 2.

8. The aqueous film-forming firefighting composition according to claim 1, wherein p and q are 1 or 2.

9. The aqueous film-forming firefighting composition according to claim 4, wherein said siloxane moiety is $(Me_3SiO)_2Si(Me)(CH_2)_3OCH_2CHOHCH_2$— or $C_4H_9Si(CH_3)_2O[Si(CH_3)_2O]_rSi(CH_2)_3OCH_2CHOHCH_2$—.

* * * * *